United States Patent [19]

Willstead

[11] 4,423,101

[45] Dec. 27, 1983

[54] ABSORBENT PRODUCTS

[75] Inventor: Donald A. Willstead, Southampton, England

[73] Assignee: Johnson & Johnson, New Brunswick, N.J.

[21] Appl. No.: 310,547

[22] Filed: Oct. 13, 1981

[51] Int. Cl.³ .................... A61L 15/00; A61L 15/01
[52] U.S. Cl. .................................. 428/76; 428/138; 428/219; 428/220; 428/304.4; 428/315.7; 428/317.3; 428/345; 428/523; 428/910; 128/156
[58] Field of Search ............... 428/137, 138, 343, 345, 428/313.3, 76, 304.4, 318.4, 219, 317.3, 315.7, 910; 128/156, 155

[56] References Cited

U.S. PATENT DOCUMENTS 3,543,750  12/1970  Meizanis ........................ 128/156

FOREIGN PATENT DOCUMENTS 1525224  9/1978  United Kingdom .
1556614  11/1979  United Kingdom .

Primary Examiner—Alexander S. Thomas

[57] ABSTRACT

The present invention relates to absorbent products such as plasters and bandages, surgical wound dressings, female sanitary protection products, baby napkins, e.g. disposable napkins, and incontinence products. An absorbent product of the invention comprises an absorbent material, at least partially faced by a cellular plastics film, preferably a polyolefin film, e.g. polyethylene film, having perforations which have been produced by passing electrical discharges therethrough. The absorbent material may be entirely embraced by the cellular plastics film, or one face of the absorbent material may be covered by the cellular plastics film and another face optionally covered by a backing sheet.

6 Claims, 9 Drawing Figures

ABSORBENT PRODUCTS

The present invention relates to absorbent products of the kind comprising absorbent material and a porous facing material, for example, plasters and bandages, surgical wound dressings, female sanitary protection products, baby napkins, e.g. disposable napkins and incontinence products.

According to the present invention there is provided an absorbent product comprising an absorbent material at least partially faced by a cellular plastics film having perforations which have been produced by passing electrical discharges therethrough. In one aspect of the invention, the absorbent material is entirely embraced by said cellular plastics film. In another aspect of the present invention, one face of the absorbent material is covered by said cellular plastics film and another face is optionally covered by a backing sheet.

A suitable cellular plastics film is described in U.K. Patent Specification No. 1,556,614 and is a thermoplastic polymeric film in which voids or cells are generated by one or more of a variety of means including
(i) the use of physical or chemical blowing agents;
(ii) the physical deformation of materials containing additives other than blowing agents which cause the material to be void-containing on physical deformation, which additives may, for example, be inorganic or organic fillers or pigments and
(iii) the leaching out of soluble additives.

Preferably the film is as described and claimed in U.K. Patent Specification No. 1,525,224. This is a stretched polyolefin film having a substantially uniform cellular structure and formed from a composition comprising a crystalline linear polyolefin, which film has at least the following characteristics:
(1) it comprises no more than 14% by volume of the film of closed cells;
(2) it has an apparent density which is 90 to 20% of the density of the non-cellular unstretched composition;
(3) it has a cell factor equal to or less than +0.65, which factor may be zero or negative;
(4) it contains from 0 to 25% by weight based on the polyolefin of a filler and/or pigment;
(5) it has a thickness of up to 11 mils; (thousandths of inch)
(6) it comprises cells with dimensions such that the average cell volume is no greater than $10^{-4}$ cc;
(7) it has been stretched in the plane of the film by an amount corresponding to a stretch ratio of at least 1.1:1 in one direction or in two substantially mutually perpendicular directions.

The mode of calculation of the percentage volume of closed cells, the apparent density, the cell factor, film thickness and average cell volume are described in the U.K. Specification 1,525,224.

The film is preferably a foamed high density polyethylene film having a weight range of 10 to 100, preferably 10 to 50 g/m$^2$ and preferably containing from 10 to 80 perforations/cm$^2$. Foamed high density polyethylene film sold under the trade name "Aerowrap" by B.X.L. Plastics Limited having a weight of about 12 or 16 g/m$^2$ and 40 perforations/cm$^2$ has been found particularly useful. The foam cell structure reduces the springiness of the film so that it folds and retains the folds well in the machine make up of the absorbent products.

The perforations may be made by the discharge method disclosed in German Offenlegungsschrift No. 2552919. This produces a spread of sizes for the perforations due to the cellular nature of the film. The range of sizes is normally between approximately 100 microns in diameter and 800 microns with preferably at least 30% of the perforations having sizes between 300 microns and 600 microns. The spark discharge perforations are preferentially formed at the voids and thin walled cells of the foam structure and thereby the perforations are neatly formed with a minimum of thermal degradation or melt displacement and with melt-smooth edges which are virtually inconspicuous and non-abrasive as they contain a minimum of displaced plastics material. The small smooth edged perforations gives good drainage of fluids into the absorbent material, whilst providing good encapsulation of the absorbent material. It has been found that this material has non-adherent wound release properties, allows the passage of blood and water through the perforations, is soft, smooth, flexible and non-abrasive, conforms wells and is not harsh or rigid in contact with the skin or wounds and is strong with good resistance to tear initiation and propagation. Also compared to previously used materials, the relative freedom from surface roughness, large holes, and perforations containing polymer webs, reduces the chance of amalgamation of the dressing to a scab or developing wound repair tissue.

It is also believed that the electrical discharge method of perforation assists in providing the permeability properties of the cellular plastics film required in absorbent products and its effect is somewhat similar to the corona electrical discharge process used to promote ink adhesion on plastics films which are to be printed. The effect of the electrical discharge is that one side of the film is lightly pitted and oxidized by the discharge and ionisation, and that surface tension is modified and the contact angle reduced. Drops of water, for example, applied to such side of the film will spread and hence penetrate the film more easily than on the other side on which water remains as discrete drops.

Accordingly the cellular film enhances passage of liquid in the direction towards the untreated side of the film. When the film is used in products, such as baby napkins, where a large volume of liquid needs to be rapidly distributed and absorbed over a large area, it is preferred that the pitted and oxidized side of the film be exposed to the liquid to be absorbed.

However when the film is used in wound dressings, it is preferred that the untreated side of the film be exposed to the blood or wound exudate to be absorbed. The blood or wound exudate is generally small in volume and more viscous and moves more slowly through the perforations. However on meeting the pitted and oxidized side of the film, the blood or wound exudate is assisted to disperse and becomes more uniformly distributed in the absorbent. It is also known that the untreated side of the film has lower adhesion to, and better releases from the wound repair tissue.

The following FIGS. 1 to 9 illustrate a number of absorbent products according to the present invention in which the perforations in the perforated cellular film have been produced by electrical discharges.

In the drawings, the same reference numerals indicate the same or similar parts.

Figure 1:
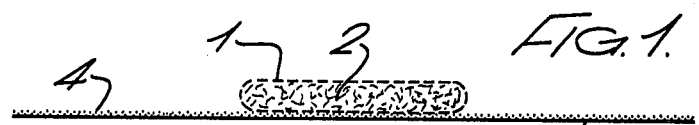
FIG. 1 shows a cross-section through an adhesive plaster or bandage.
Figure 2:
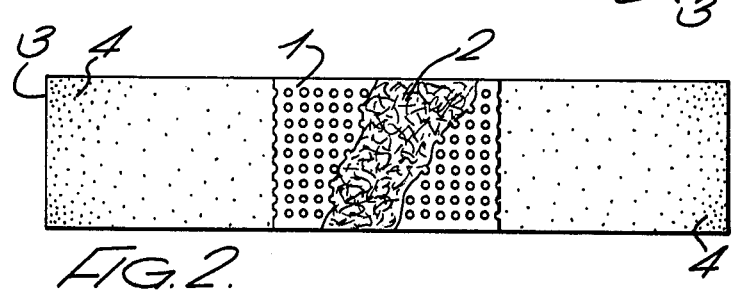
FIG. 2 is a plan view of FIG. 1.

Referring to FIGS. 1 and 2 there is shown an adhesive plaster or bandage comprising a backing sheet 3 having a layer of pressure sensitive adhesive 4 thereon. A layer, such as a pad, of absorbent material 2 is entirely embraced by a perforated cellular plastics film 1. In use, the plaster is placed over the wound with the perforated film 1 in contact with the wound.

Preferably the cellular plastics film is of the foamed type such as described and claimed in British Patent Specification No. 1,525,224 or described in British Patent Specification No. 1,556,614, and is preferably a foamed high density polyethylene film having a weight range of 10 to 100, preferably 10 to 50, g/m$^2$ and preferably containing from 10 to 80 perforations/cm$^2$. Foamed high density polyethylene film sold under the trade name "Aerowrap" by B.X.L. Plastics Limited having a weight of about 12 or 16 g/m$^2$ and 40 perforations/cm$^2$ has been found particularly useful.

Figure 3:
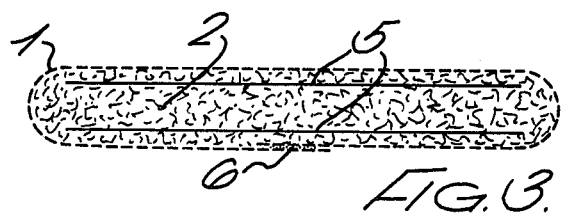
FIGS. 3 to 6 show cross-sections of various surgical wound dressings.
Figure 4:
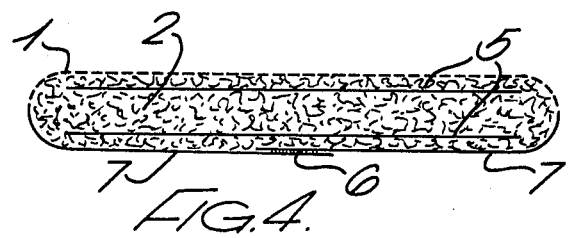
Figure 5:
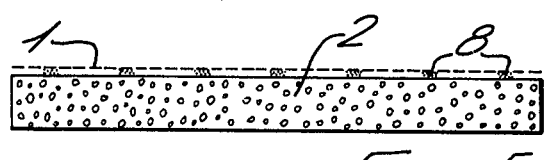
Figure 6:
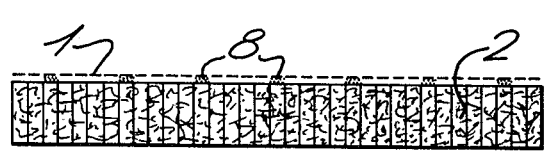

Referring to FIGS. 3 to 6 there are shown various surgical wound dressings. In FIG. 3, a pad of absorbent material 2 (such as cotton or rayon fibres) is embraced by a sheet of perforated cellular plastics film 1 having its ends joined by adhesive 6. Within absorbent material 2 are two layers of semi-repellent tissue 5. In FIG. 4, absorbent material 2 is covered on one face by a perforated portion 1 and on the other face by a non-perforated portion or backing sheet portion 7 of a sheet of plastics film. Again the ends of plastics film are joined by adhesive 6 and within absorbent material 2 are two layers of semi-repellent tissue 5. In FIGS. 5 and 6 perforated plastics film is mounted over one face of absorbent material 2 by lines of adhesive 8. The absorbent material 2 may be foam (as in FIG. 5) or needle-loomed or felted cotton or rayon (as in FIG. 6). In use, the wound dressings described in FIGS. 3 to 6 are placed on the wound with the perforated cellular film in contact with the wound.

Figure 7:
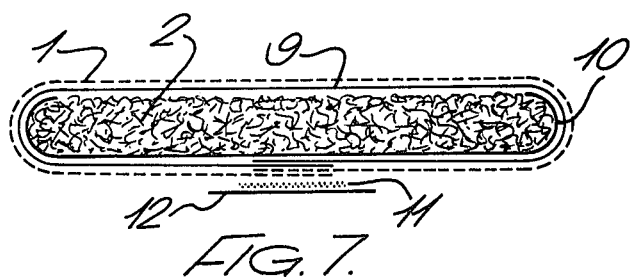
FIGS. 7 and 8 show cross-sections of female sanitary protection products.

In FIG. 7, the pad of absorbent material 2, such as woodpulp, is partially embraced by a plastics film 10 for retaining absorbed fluid. The absorbent material 2 and plastics film 10 is wholly embraced by a layer of tissue 9 which in turn is embraced by a perforated plastics film 1. The ends of the tissue and the ends of the film 1 overlap as shown and are secured by known means. An attachment layer of pressure sensitive adhesive 11 is secured to the underside of the perforated plastics film 1 and a layer of silicone coated release paper 12 protects the adhesive before use.

Figure 8:
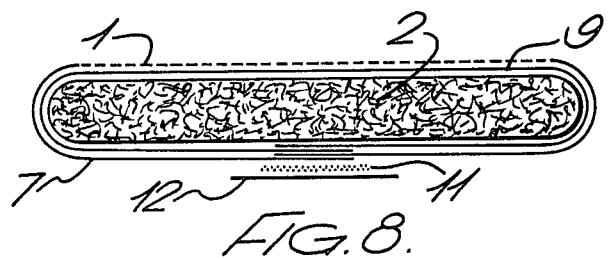

In FIG. 8, a layer pad of absorbent material 2, such as woodpulp is wholly embraced by a layer of tissue 9. The tissue layer 9 is covered on one face by a perforated portion of plastics film 1, and on the opposite face by a non-perforated portion, or backing sheet portion 7 of said film 1. An attachment layer strip of pressure sensitive adhesive 11 is secured to the underside of the backing sheet portion 7, and a layer of silicone release paper 12 protects the adhesive before use. In use the female sanitary protection products of FIGS. 7 and 8 are secured to panties by means of adhesive 11.

Figure 9:
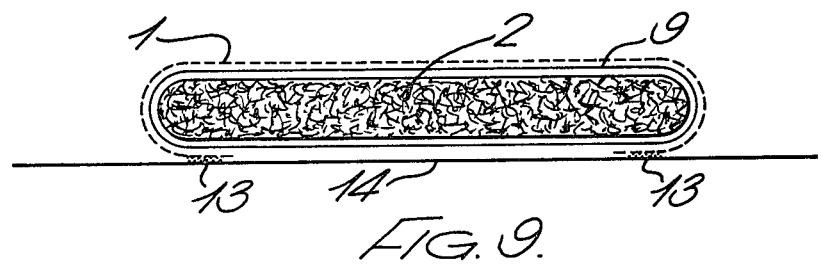
FIG. 9 shows a cross-section of a baby napkin.

In FIG. 9, a pad or absorbent material 2, such as woodpulp, is wholly embraced by tissue 9 which in turn is embraced by perforated plastics film 1. The perforated plastics film 1 is attached to a non-perforated plastics backing sheet 14 by means of adhesive 13.

The present invention also relates to the use of electrical discharge perforated cellular plastics films (particularly as claimed and described in British Pat. Nos. 1,515,224 or 1,556,614) for surgical drapes and gowns, and disposable protective clothing.

The present invention also relates to the use of electrical discharge perforated cellular plastics films (particularly as claimed and described in British Pat. Nos. 1,525,224 or 1,556,614) for filtrations media, such as face masks. The film can be used in a mask of the type in which a fibrous layer is embraced between two outer support layers of film. Furthermore it has been found possible to provide a face mask from a number of superimposed layers of the perforated film, e.g. four superimposed perforated layers of 16 g/m$^2$ film. It is believed that it is possible to breath through a plurality of layers of this film because the irregular foamed surfaces provide air channels between film layers. Such a face mask is low in cost and is particularly useful in coarse dust atmospheres.

As mentioned hereinbefore, the electrical discharge method of perforation enhances passage of liquid in the direction towards the untreated side of the film. This property is essential in films used as nappy liners. Accordingly the invention also comprehends the use, as a nappy liner, of electrical discharge perforated cellular film (particularly as claimed and described in British Patent Specifications Nos. 1,525,224 or 1,556,614). In use, the nappy liner is inserted between the baby's body and the nappy.

The present invention also relates to the use of electrical discharge perforated cellular plastics films (particularly as claimed and described in British Pat. Nos. 1,515,224 or 1,556,614) for hospital disposable examination drapes and gowns. The air and moisture vapour permeability properties conferred on the cellular film by the perforations permit drapes and gowns to be fabricated which are comfortable to wear since the normal skin transpiration functions are not impeded. The non-reflected light glare and non-transparent modesty characteristics required in drapes and gowns are conferred by the light diffusion properties of the irregular cellular film surface but these characteristics are preferably enhanced by the incorporating opacifying fillers and/or pigments into the plastic matrix from which the cellular film is originally produced.

The present invention also relates to the use of electrical discharge perforated plastics film (particularly as claimed and described in British Pat. Nos. 1,515,224 or 1,556,614) in incontinence products.

I claim:

1. An absorbent product comprising an absorbent material for retaining absorbed fluid at least partially faced by a cellular plastic film having perforations which have been produced by passing electrical discharges therethrough, said film having at least the following characteristics:
   (a) it comprises no more than 14% by volume of the film of closed cells;
   (b) it has an apparent density which is 90 to 20% of the density of a non-cellular unstretched composition;
   (c) it has a cell factor equal to or less than +0.65, which factor may be zero or negative;
   (d) it contains from 0 to 25% by weight based on the polyolefin of the filler and/or pigment;

(e) it has a thickness of up to 11 mils;
(f) it comprises cells with dimensions such that the average cell volume is no greater than $10^{-4}$ cc;
(g) it has been stretched in the plane of the film by an amount corresponding to a stretch ratio of at least 1.1:1 in one direction or in two substantially mutually perpendicular directions;
said perforated film being pitted and oxidized by the electrical discharges, and the pitted and oxidized side of the film facing said absorbent material.

2. An absorbent product according to claim 1 comprising a backing sheet having a layer of pressure sensitive adhesive thereon, and a layer of absorbent material entirely embraced by a perforated cellular plastics film on said pressure sensitive adhesive.

3. An absorbent product according to claim 1 wherein said polyolefin film is a polyethylene film.

4. An absorbent product according to claim 1 wherein said film has a weight range of 10 to 100 g/m$^2$.

5. An absorbent product according to claim 1 wherein said film has a weight range of 10 to 50 g/m$^2$.

6. An absorbent product according to claim 1 wherein said film contains from 10 to 80 perforations/cm$^2$.

* * * * *